United States Patent
Popescu

(10) Patent No.: US 7,792,231 B2
(45) Date of Patent: Sep. 7, 2010

(54) METHOD AND APPARATUS FOR TRANSFER OF MULTIPLE DATA STREAMS ACCUMULATING IN PARALLEL BETWEEN TWO UNITS MOVING RELATIVE TO EACH OTHER

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 508 days.

(21) Appl. No.: 11/856,753

(22) Filed: Sep. 18, 2007

(65) Prior Publication Data

US 2008/0075213 A1    Mar. 27, 2008

(30) Foreign Application Priority Data

Sep. 21, 2006    (DE) .................... 10 2006 044 660

(51) Int. Cl.
*H04L 7/00* (2006.01)
(52) U.S. Cl. ........................................ 375/354
(58) Field of Classification Search ............. 375/285, 375/354–355, 377; 378/98
See application file for complete search history.

(56) References Cited

U.S. PATENT DOCUMENTS

| | | | |
|---|---|---|---|
| 5,530,422 A | 6/1996 | Harrison | |
| 5,530,425 A | 6/1996 | Harrison | |
| 7,212,101 B2 * | 5/2007 | Lohr | 340/310.17 |
| 7,248,641 B2 | 7/2007 | Schilling et al. | |
| 7,421,058 B2 * | 9/2008 | Popescu et al. | 378/20 |
| 7,425,096 B2 * | 9/2008 | Beyerlein et al. | 378/203 |
| 7,599,445 B2 * | 10/2009 | Schilling et al. | 375/285 |
| 2002/0150045 A1 | 10/2002 | Vogtmeier et al. | |
| 2003/0095263 A1 * | 5/2003 | Varshneya et al. | 356/477 |
| 2005/0231836 A1 | 10/2005 | Schilling et al. | |
| 2006/0256634 A1 | 11/2006 | Krumme | |
| 2007/0063785 A1 | 3/2007 | Krumme et al. | |

FOREIGN PATENT DOCUMENTS

| | | |
|---|---|---|
| DE | 10 2004 051 170 | 5/2006 |
| EP | 1 051 816 B1 | 5/2002 |

OTHER PUBLICATIONS

IEEE Std 802.11 (2005).
"Kanalcodierung," Friedrichs (1995) pp. 1-8.
"Taschenbuch der Hochfrequenztechnik," Meinke et al (1968) p. 1396.
"Specification of the Bluetooth System" (2004).

* cited by examiner

*Primary Examiner*—Khanh C Tran
(74) *Attorney, Agent, or Firm*—Schiff Hardin LLP

(57) ABSTRACT

In a method and a device for transfer of a number of digital data streams accumulating in parallel between units moving relative to one another, the digital data to be transferred are modulated at least partially to avoid excessively high interference radiation. The data are transferred serially between the units (16, 18) and the data are demodulated after the transfer. The data accumulating in parallel and to be transferred are divided up into a number of data sets; the potential or actual tendency for generation of EMI radiation is examined for each data set. A modulation pattern is selected for each data packet dependent on the degree of the tendency to generate EMI radiation, with modulation pattern the EMI radiation arising in the data transfer in connection with the respective data set is largely reduced. Each data set is modulated according to the selected modulation pattern before the transfer.

22 Claims, 3 Drawing Sheets

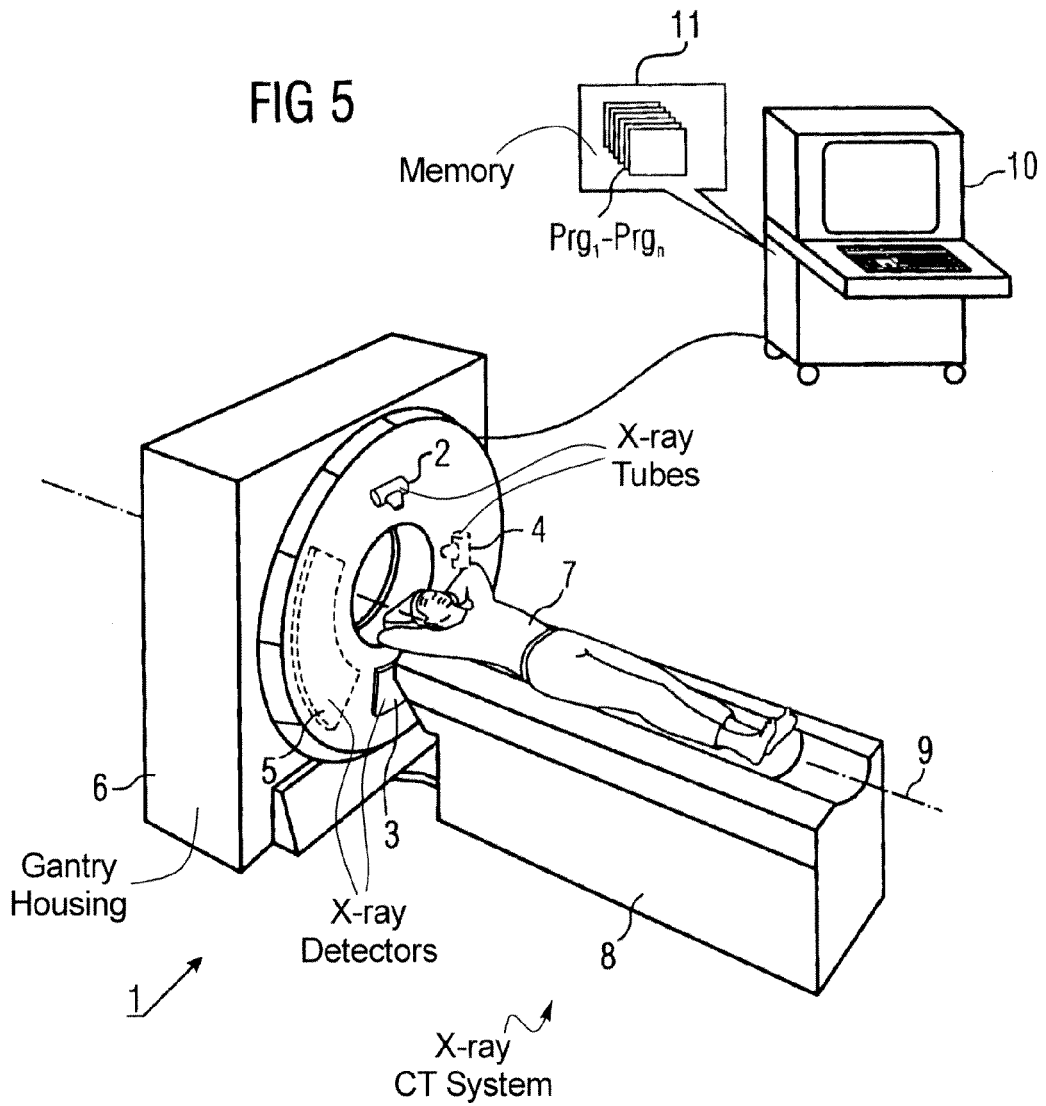

METHOD AND APPARATUS FOR TRANSFER OF MULTIPLE DATA STREAMS ACCUMULATING IN PARALLEL BETWEEN TWO UNITS MOVING RELATIVE TO EACH OTHER

BACKGROUND OF THE INVENTION

1. Field of the Invention

The present invention concerns a method and a device for transferring a number of data streams accumulating in parallel between units moving relative to one another, the digital data to be transferred being modulated so as to make the data at least somewhat resistant to generating interfering radiation, the data being transferred serially between the units and the data being demodulated after the transfer.

2. Description of the Prior Art

In the transfer of high data quantities, the problem of excessively high EMI (electromagnetic interference) radiation frequently occurs arise since the transferred data exhibit certain regularities that lead to the situation of high interference radiation arising in specific frequency ranges. Such interference radiation can negatively influence the operation of other apparatuses, or, possibly to the point of failure, such that it is necessary to keep this EMI radiation optimally low. Electromagnetic compatibility (EMC) standards exist for this purpose. This is in particular the case for medical apparatuses that are used in the environment of hospitals and clinics since here vital apparatuses could be disrupted in terms of their function.

At present this requirement inhibits the steadily growing quantity of data to be transferred in apparatuses such as, for example, computed tomography apparatuses, since this EMI problem becomes more severe as the data quantity increases.

WO 2004/032364 A1 and EP 1 051 816 B1 disclose approaches for reducing the EMI radiation in the data transfer between moving units can be achieved by an encoding of the data stream by encoding of transferred data therein.

European Patent EP 1 051 816 B1 describes a method for low-interference signal transfer of a digital signal from a transmitter to a spatially separated receiver, wherein a modulation unit modulates the entire signal to be transferred. It is necessary to design an additional transfer path between the transmitter and receiver with which a synchronization signal between the transmitter and the receiver can be transferred in order to be able to implement the demodulation of the modulated signals at the receiver in the correct manner.

A method for broadband transfer of digital signals in which the signals to be transferred are likewise encoded is known from WO 2004/032364 A1, wherein it is sought to adapt to the actual EMC situation by selecting different modulations that, for example, can be varied dependent on electrical measurement variables, in particular the currently measured interference level. The entire transferred signal is also encoded so that a separate transfer path for transfer of a synchronization signal for correct decoding of the transferred, encoded signals is necessary. Moreover, these methods have the disadvantage is that a reaction to the electromagnetic EMI radiation can occur only if it was actually measured.

SUMMARY OF THE INVENTION

An object of the invention is to provide an improved method for transfer of a number of digital data streams accumulating in parallel and a corresponding data transfer device, which can forego a parallel synchronization path for synchronization of encoding and decoding and that can adapt to the property of the data to be transferred so that momentary electromagnetic emissions are avoided.

The invention is based on the insight that a significantly more advantageous situation with regard to the EMI radiation can be achieved when the actual data packets to be sent are examined (inspected) separately as to their potential tendency for generation of electromagnetic radiation, before the actual employed pattern for encoding of the respective data set is selected, since it can occur that the electromagnetic radiation is amplified instead of reduced due to the additionally-effected modulation, and the possibility exists to generate optimal interference radiation suppression by adaptation of the employed modulation pattern to the respectively transmitted data sets.

Furthermore, the invention is based on the insight that it is more advantageous to individually modulate the respectively transmitted data sets, so the data packets that are subsequently transferred between the transmitter and receiver in a serial manner should include unmodulated synchronization signals or synchronization data so that no additional unsynchronized transfer path is necessary.

Based on these insights, in a method according to the invention for transfer of a number of digital data streams accumulating in parallel between units moving relative to one another, the digital data to be transferred are at least partially modulated to avoid excessively high interference radiation; the data are transferred serially between the units; and the data are demodulated after the transfer. According to the invention, this known method is improved by the data accumulating in parallel and to be transferred being divided into a number of data sets that are transferred in integrated form in data packets, the potential or actual tendency for generation of EMI radiation being examined for each data set before the transfer, and a modulation pattern being selected per data packet dependent on the degree of the tendency to generate EMI radiation, with which modulation pattern the EMI radiation arising in the data transfer in connection with the respective data set is largely reduced, and subsequently each data set is modulated according to the selected modulation pattern before the transfer thereof.

In this manner it is possible to individually adapt the modulation to the actual data to be transferred, such that an optimally slight interference radiation arises in the transfer itself.

For example, a Fourier analysis of the data set can be implemented for such an examination with regard to the potential tendency of the data set towards generation of interference radiation. It is also possible to determine this potential tendency for generation of interference radiation by the generation of a histogram of the data set. Such a histogram describes the frequency of the occurrence of the same values in the data set as amplitude bars.

Each data set can inventively be inserted in the modulated state into a data packet which additionally has an unmodulated data attachment. The data packets can be transferred serially between the transmitter and receiver, so a separate synchronization line is no longer necessary.

Such an unmodulated data attachment can be arranged, for example, at the beginning of the data packet, and the unmodulated data attachment can include a synchronization bit sequence, advantageously a synchronization data word.

Furthermore, the unmodulated data attachment at the beginning of the data packet can contain information with regard to the modulation pattern of the data set, and an identical pattern generator for generation of the modulation pattern can be used both at the transmitter side and at the receiver side and a bit pattern, or a number that initializes the pattern generator, is transferred as information with regard to the modulation pattern.

Furthermore, each data packet can contain at least one item of error protection information that is either in the modulated part of the data packet or in the unmodulated part of the data packet. This can be a CRC bit sequence (a cyclical block check) and/or an FEC bit sequence (a forward error correction).

Error protection information can also be provided in the region of the modulated data and additionally in the region of the unmodulated data.

If data packets of different data length are transferred, it can be advantageous to pad unused data sets with empty data, which should advantageously be modulated since a longer, identical bit sequence could in lead to increased interference radiation.

In an embodiment of the invention, a modulation pattern is provided and a modulation with this one modulation pattern is implemented, or no modulation is implemented, per data set, corresponding to the degree of the potential tendency for generation of EMI radiation.

According to a further embodiment, a predetermined number of specific modulation patterns is provided and a first modulation pattern is applied to at least one part of every data set, and it is decided from the result of the modulation whether the modulation is sufficient to sufficiently reduce the EMI radiation due to this data set; and this data set is implemented with this modulation type in the data packet if it produces sufficient suppression of the EMI radiation while, if it is determined to produce insufficient suppression of the EMI radiation, this data set is processed with another modulation pattern, with new modulation patterns being selected until a sufficient suppression of the EMI radiation occurs.

If all present modulation patterns are worked through and no sufficient suppression of the EMI radiation is achieved, the last-used modulation pattern, or that modulation pattern that exhibits the best suppression of the EMI radiation, can be used, for example.

In this procedure according to the invention, for the next examined data set, the first modulation attempt is begun with the modulation pattern of the last modulation type of the preceding data set. It is assumed that the sequentially examined data sets normally do not differ stochastically in terms of their basic structure, but rather that "adjacent" data sets exhibit similar basic structures.

In another embodiment of the inventive method, a number of different modulation patterns are applied to at least one part of each data set, and the strongest amount of expected EMI radiation is determined for each pattern, and this data set, modulated with the most advantageous modulation pattern, is implemented in the data packet.

In another embodiment of the inventive method, at least one part of each data set is examined (with regard to its spectral distribution) for the potential to generate EMI radiation upon serial data transfer, the correct modulation pattern for optimal suppression of this EMI radiation is determined, and this data set, modulated with this most advantageous modulation pattern, is implemented in the data packet.

Furthermore, a modulation pattern having a length greater by multiple powers of ten than the length of the data sets to be modulated or the transferred data packets is used in a further embodiment.

Moreover, it is possible for a number of data sets to be packed into a data packet.

The method described above is particularly suitable for transfer of detector data in a computed tomography system,
advantageously an x-ray CT system. Moreover, control data also can be transferred in this manner within the computed tomography system. Furthermore, the transfer of the signals between the transmitter and receiver can occur wirelessly at least over a portion of the length of the transfer path and via at least one sliding contact, for example via slip rings of a gantry of a CT system.

The above object also is achieved in accordance with the invention by a data transfer device for transfer of a number of digital data streams accumulating in parallel between units moving relative to one another. This data transfer device has a buffer memory for parallel storage of a number of data sets of different specification that accumulate in parallel, and a packet processor that individually examines the data sets transferred from the buffer memory for a potential or actual tendency to generate EMI radiation and, dependent on the degree of the tendency to generate EMI radiation, that select for each data packet a modulation pattern with which the EMI radiation arising in the data transfer in connection with the respective data set is largely reduced, and inserts the data set, modulated with the selected modulation pattern, into the data packet. A serializer which processes the data packets accumulating in parallel into a serial data stream composed of a number of data packets. A transmitter transfers or transmits the serialized data and a receiver receives the transferred or transmitted data. A de-serializer restores the parallel streams from the serial data stream. A packet processor extracts the data sets and demodulates the data sets. A cache memory buffers the demodulated data sets until further processing.

Such a data transfer device, for example, can be part of a computed tomography system, in particular an x-ray CT system. The units rotated relative to one another can be the rotor and stator of a gantry of such a CT system.

Furthermore, computer processors and a memory can be provided in this data transfer device in which program code (data structure) is stored centrally or decentralized, the program code causing the computer processors to implement the method explained above.

The transmission path can include a wireless portion for transfer of the signals between the transmitter and receiver, or at least one sliding contact can be arranged in the transmission path between the transmitter and receiver.

BRIEF DESCRIPTION OF THE DRAWINGS

FIG. 5 shows an x-ray CT system with an inventive data transfer device.

DESCRIPTION OF THE PREFERRED EMBODIMENTS

Figure 3:
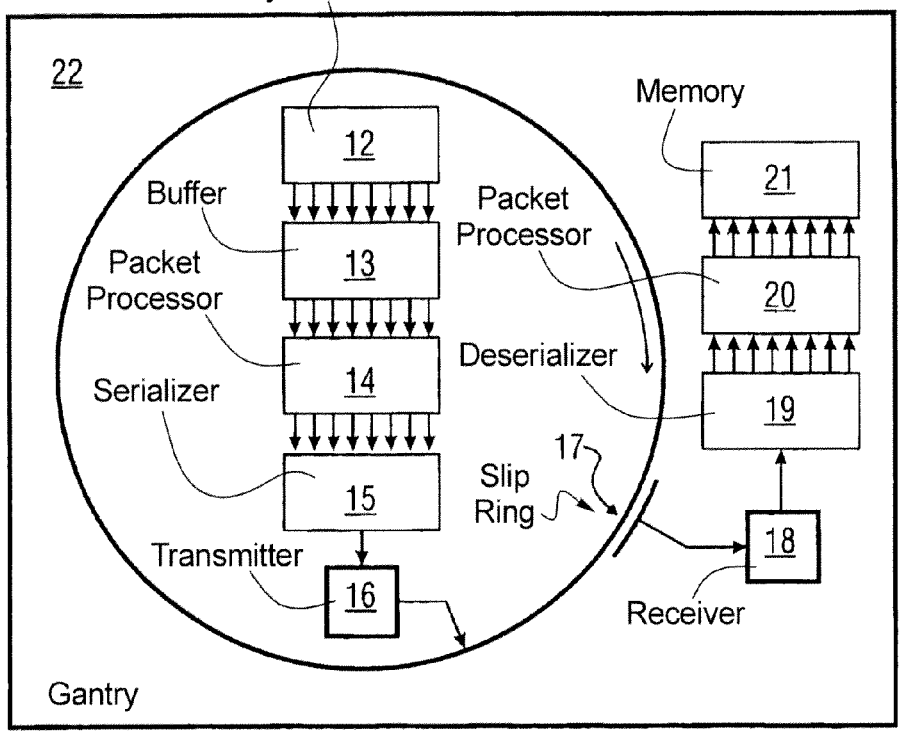
FIG. 3 schematically illustrates the flow of the inventive modulation method.
Figure 4:
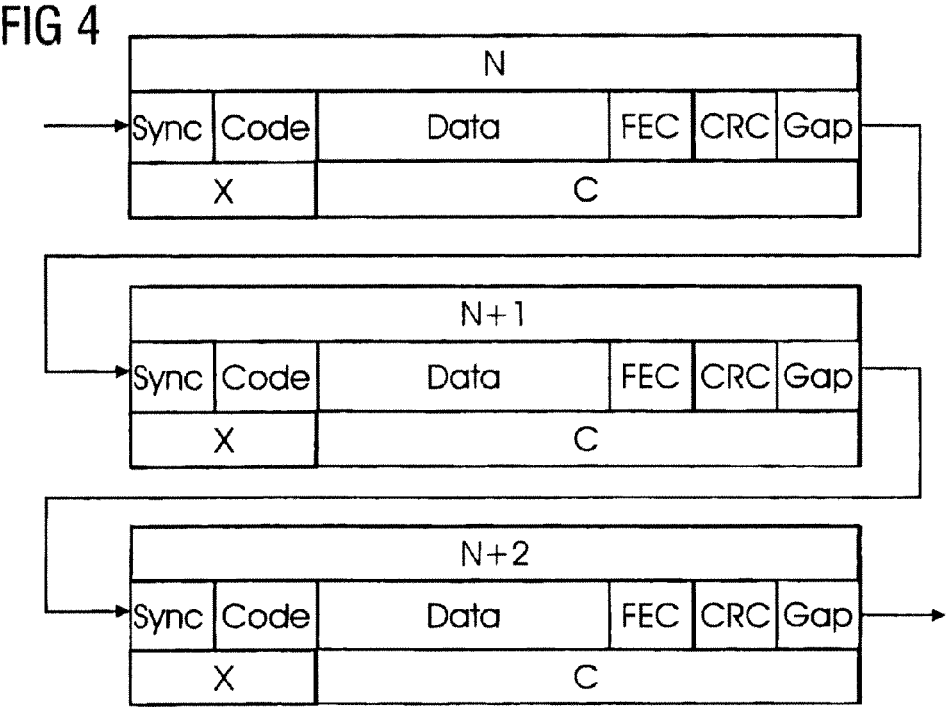
FIG. 4 illustrates the inventive data packet format for transfer of modulated data.

FIGS. 3, 4 and 5 show only the features necessary for understanding of the invention are shown. The following reference characters are hereby used: 1: x-ray CT system; 2: first x-ray tube; 3: first detector; 4: second x-ray tube; 5: second detector; 6: gantry housing; 7: patient; 8: patient bed;

9: system axis; 10: computation and control unit; 11: memory; $Prg_1$ through $Prg_n$: computer programs; 12: measurement unit of the detector system; 13: buffer; 14: packet processor; 15: serializer; 16: transmitter; 17: contact-less slip ring; 18: receiver; 19: de-serializer; 20: packet processor; 21: memory; 22: gantry; N, N+1, N+2: number of the serially transferred data packets; Sync: synchronization bit sequence; Code: modulation encoding; Data: data set; FEC: forwards error correction; CRC: cyclical block check (=cyclic redundancy checksum); Gap: data gaps; X: region of the data without modulation; C: region of the data with modulation.

Figure 1:
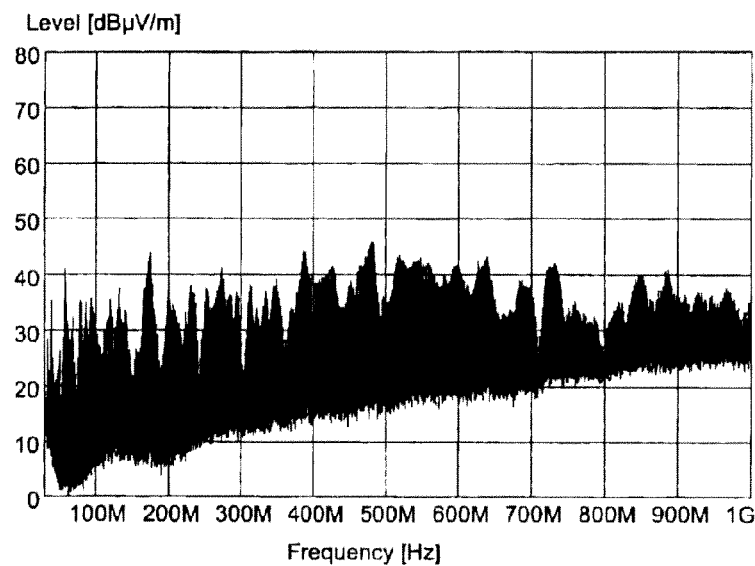
FIG. 1 shows a typical radiation profile of an individual, contact-free, capacitive or inductive slip ring in a CT system for a transfer of random number sequences at a transfer rate of 1.25 Gbps.

FIG. 1 shows a typical measured radiation profile for the transfer of random data via contact-less slip ring contacts of a computer tomography system at a data transfer rate of 1.25 Gbps. As can be seen from FIG. 1, radiation profiles with peak-like resonances typically arrive at specific frequencies due to this data transfer, and the position and height of the individual peaks is difficult to predict and depends on a large number of variables that cannot be influenced, such as the smallest changes in the structure of a gantry, fabrication tolerances, and the like. Such resonances of the radiation profile have a very disruptive effect with regard to the EMI compatibility of an apparatus and should be excited as seldom as possible.

Figure 2:
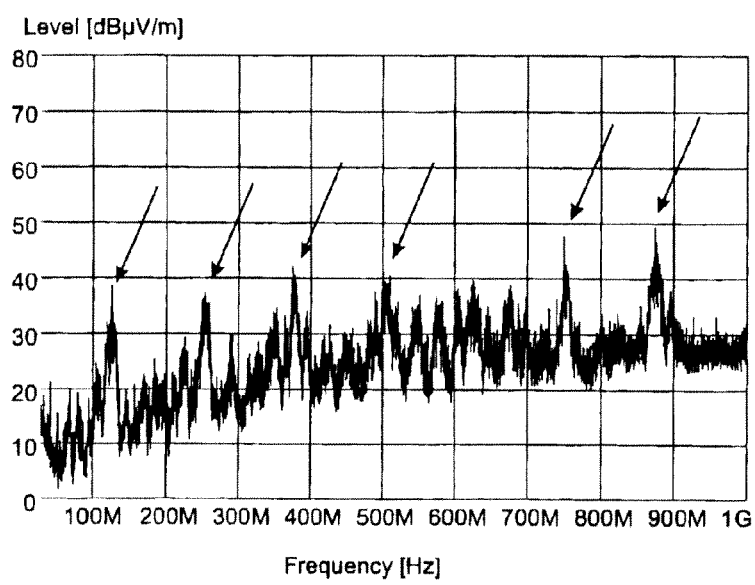
FIG. 2 shows the spectral power distribution of a transferred measurement data stream given a transfer rate of 1.25 Gbps.

FIG. 2 shows the spectral content of a number sequence as occurs, for example, in the transfer of detector data of a CT system. Here the spectral peaks (characterized by the angled arrows) can be seen that lead to radiation peak in the respective frequency spectrum when the data are transferred unmodulated within a CT system. These radiation peaks can possibly excite the resonances and lead to higher EMI levels. The distribution of such data is highly dependent on the examined subject. This means that completely different data exist if small subjects (for example a hand or a head) are examined compared with large subjects (for example the cross-section of a voluminous patient). Furthermore, the type of the data and their spectral distribution (with their spatial resonances and radiation peaks resulting therefrom) also depend on the angle position of the gantry. It cannot be predicted, however, how the radiation spectrum will develop in the course of a spiral CT scan.

The object of the invention is thus primarily to recognize such overshoots in the radiation spectrum (and therewith first in the data spectrum) and to avoid them by an appropriate modulation in the data transfer of the detector data to the computer system or to the data evaluation system.

FIG. 3 shows the flow scheme of such an inventive data transfer, wherein in the detector system 12 the parallel data streams are transferred into a digital memory 13. From this digital memory 13 the data (likewise in parallel) are relayed to a packet processor 14 in which every data set is handled and optimally modulated in parallel corresponding to the rules of the method described above. A transfer (likewise still in parallel) to a serializer 15 subsequently follows with the data sets (which have been modulated in the meanwhile) originating from the packet processor 14 being embedded into data packets. All of the data packets have corresponding synchronization information and information regarding the type of the data encoding, which information is itself not encoded.

These data packets created in this manner are serially relayed to the transmitter 16 that relays the data to a receiver 18 via a contact-free slip ring 17 within the gantry 22. The receiver 18 passes these data to a de-serializer 19 in which the packet boundaries are detected using the synchronization bit sequences and the data are restored to parallel streams again and relayed to the packet processor 20. The individual data packets that exist still modulated in this state additionally include the respective modulation code applicable for the corresponding packet, such that the packet processor 20 can effect the demodulation with the correct modulation pattern and can relay the demodulated data to a memory unit 21.

FIG. 4 shows the exemplary design of three data packets N through N+2, whereby the design of the data packets is fundamentally identical. Each data packet begins with an un-encoded synchronization information "Sync" followed by an encoding information "Code". The data forming both these information items are un-modulated, as represented by the "X" situated below. The actual data set that was modulated by the packet processing follows after these. The error correction bit sequences "FEC" and "CRC", likewise modulated, finally follow. The data space still free can be closed by a bit sequence "Gap", likewise modulated. The data that are modulated are designated with "c" situated below. After the end of a data packet (which, in the example shown, always has a constant data length), the next data packet comes, etc.

It should be noted that the structure of the data packets can be designed differently. For example, a further error correction value can be inserted at the end of the encoded data sequence or the error correction values can be transferred un-encoded overall. The possibility also exists to transfer the code information at another point of the data packet and similar measures.

FIG. 5 now shows such an x-ray CT system in which an inventive data transfer device for transfer of the detector data from the two detectors 3 through 5 to the computation and control unit 10 is installed in the gantry housing 6.

The CT system shown here has a displaceable patient table 8 on which is located a patient 7 who can be inserted into the scan field of the gantry, whereby the focus detector systems 2, 3 and 4, 5 run over the scan field. The control and reconstruction of the images ensues via a control and computation unit 10 in which programs $Prg_1$ through $Prg_n$ are also located in a memory 11, which programs $Prg_1$ through $Prg_n$ implement the control and the actual reconstruction. Program code can also be located in such a memory 11 that is transferred to processors of the data transfer device upon the initialization of the CT system, or such a program code can exist permanently in the corresponding processors.

Although modifications and changes may be suggested by those skilled in the art, it is the intention of the inventors to embody within the patent warranted hereon all changes and modifications as reasonably and properly come within the scope of their contribution to the art.

I claim as my invention:

1. A method for transferring digital data between units that are moving relative to one another, said digital data accumulating in parallel at one of said units, said method comprising the steps of:

at said one of said units, dividing the data accumulating in parallel, and to be transferred to the other of said units, into a plurality of data sets, respectively to be transferred in data packets;

at said one of said units, inspecting each data set as to its potential or actual tendency for generation of electromagnetic interference (EMI) radiation and, for each data packet, selecting a modulation pattern therefor, dependent on a degree of its tendency to generate EMI radiation, that will substantially reduce said EMI radiation arising upon transfer of that data set;

at said one of said units and before transferring each data set, modulating each data set with the modulation pattern selected therefor, thereby producing modulated data sets;

transferring the modulated data sets in respective data packets from said one of said units to the other of said units; and at said other of said units, demodulating the modulated data in the respective data packets.

2. A method as claimed in claim 1 comprising determining said tendency for generating EMI radiation by implementing a Fourier analysis on each of said data sets.

3. A method as claimed in claim 1 comprising determining said tendency for generation of EMI radiation by generating a histogram for each data set describing a frequency occurrence of same values in that data set.

4. A method as claimed in claim 1 comprising inserting each modulated data set into a data packet that additionally contains unmodulated data as an attachment to the modulated data set.

5. A method as claimed in claim 4 comprising attaching said unmodulated data as an attachment at a beginning of the modulated data packet and in said unmodulated data attachment, including information selected from the group consisting of a synchronization bit sequence and an identification of the modulation pattern used to modulate the modulated data set.

6. A method as claimed in claim 5 comprising generating said modulation pattern at said one of said units with a first pattern generator and generating a demodulation pattern at said other of said units using a second pattern generator identical to said first pattern generator, and informing said second pattern generator of the modulation pattern used by said first pattern generator to produce the modulated data set in a data packet by said information in said unmodulated data attachment.

7. A method as claimed in claim 5 comprising including in each data packet at least one item of error protection information in a modulated portion of that data packet or in an unmodulated portion of that data packet.

8. A method as claimed in claim 7 comprising, as said error protection information, using a bit sequence selected from the group consisting of a cyclic redundancy checksum (CRC) bit sequence and a forward error correction (FEC) bit sequence.

9. A method as claimed in claim 1 comprising embodying each modulated data set in a data packet having a predetermined length and filling any unused spaces in said data packet of predetermined length with empty data.

10. A method as claimed in claim 1 wherein the step of selecting said modulation pattern comprises selecting at least one modulation pattern, or not selecting any modulation pattern at all, and thereby not modulating said data set, dependent on said degree of said tendency for generating EMI radiation.

11. A method as claimed in claim 1 wherein the step of selecting a modulation pattern comprises making a plurality of predetermined modulation patterns available and selecting one of said predetermined modulation pattern, as a selected modulation pattern, dependent on the degree of said tendency for generation of EMI radiation of that data set, and modulating that data set with the selected modulation pattern.

12. A method as claimed in claim 1 wherein the step of selecting a modulation pattern comprises, for each data set:
from among a plurality of predetermined modulation patterns, modulating at least a portion of the data set with a first modulation pattern from among said plurality of predetermined modulation patterns, thereby obtaining a modulation result;
automatically determining whether said modulation result sufficiently reduces the EMI radiation that will be generated by the data set upon transfer thereof;
modulating the data set with said first modulation pattern if said modulation result sufficiently reduces said EMI radiation; and
if said first modulation result does not sufficiently reduce said EMI radiation, modulating at least a portion of the data set with another of said modulation patterns in said plurality of predetermined modulation patterns until sufficient reduction of the EMI radiation that will be emitted by the data set upon transfer thereof is achieved.

13. A method as claimed in claim 1 wherein the step of selecting said modulation pattern comprises, for each data set;
applying a plurality of different modulation patterns to at least one part of the data set;
identifying the EMI radiation that will be produced by the data set upon transfer thereof for each of said different modulation patterns; and
modulating the data set with one of said different modulation patterns that will cause the data set to produce a lowest EMI radiation during transfer thereof.

14. A method as claimed in claim 13 comprising selecting the respective modulation patterns for the respective data sets in a succession of said data sets and, for a data set following a preceding data set, beginning selection of the modulation pattern for the following data set using, as said first modulation pattern, the modulation pattern that sufficiently reduced the EMI radiation for the preceding data set.

15. A method as claimed in claim 1 wherein each data set has a spectral distribution, and wherein the step of selecting a modulation pattern comprises, for each data set:
evaluating at least a portion of the spectral distribution of the data set to determine EMI radiation that will be generated by the data set upon serial transfer thereof;
automatically determining a modulation pattern that suppresses said EMI radiation upon said serial transfer; and
modulating the data set with said modulation pattern that suppresses said EMI radiation.

16. A method as claimed in claim 1 comprising employing a modulation pattern having a length that is larger by multiple powers of ten than a length of the data set modulated by that data pattern.

17. A data transfer apparatus for transferring digital data between a first location and a second location that are moving relative to one another, comprising:
a communication path between said first and second locations;
a buffer memory at said first location that stores said digital data accumulating in parallel at said first location;
a packet processor at said first location, having access to said buffer memory, that divides the data accumulating in parallel into a plurality of data sets;
said packet processor inspecting each data set as to its potential or actual tendency for generation of electromagnetic interference (EMI) radiation and, for each data set, selecting a modulation pattern therefor, dependent on a degree of its tendency to generate EMI radiation, that will substantially reduce said EMI radiation arising upon transfer of that data set;
said processor modulating each data set with the modulation pattern selected therefor, thereby producing modulated data sets, and inserting the modulated data sets into respective data packets;
a serializer at said first location, connected to said packet processor, that serializes the data packets;

a transmitter at said first location, connected to said serializer, that serially transmits the data packets via said transmission path from said first location to said second location;

a receiver at said second location that receives the transmitted data packets via said transmission path from said first location;

a de-serializer at said second location, connected to said receiver, that de-serializes the received data packets; and a further packet processor at said second location, connected to said de-serializer, that demodulates the respective data sets in the data packets and makes the demodulated data sets available at an output.

18. A data transfer apparatus as claimed in claim 17 wherein said first and second locations are locations in a computed tomography system.

19. A data transfer apparatus as claimed in claim 18 wherein said first location and said second location exhibit a relative rotation therebetween in said computed tomography system.

20. A data transfer apparatus as claimed in claim 19 wherein said first location is a stator of a gantry of said computed tomography system and wherein said second location is a rotor of said gantry.

21. A data transfer apparatus as claimed in claim 17 wherein said communication path comprises at least a portion that is wireless.

22. A data transfer apparatus as claimed in claim 17 wherein said communication path comprises at least one sliding contact between said transmitter and said receiver.

* * * * *